United States Patent [19]

Takayama et al.

[11] Patent Number: 4,517,125
[45] Date of Patent: May 14, 1985

[54] NOVEL VITAMIN $D_3$ DERIVATIVES AND PROCESS FOR PRODUCING THE SAME

[75] Inventors: Hiroaki Takayama; Sachiko Yamada; Keiko Nakayama; Tatsuo Suda, all of Tokyo, Japan

[73] Assignee: Chugai Seiyaku Kabushiki Kaisha, Tokyo, Japan

[21] Appl. No.: 463,616

[22] Filed: Feb. 3, 1983

[51] Int. Cl.³ .................................................. C07J 9/00
[52] U.S. Cl. ...................................... 260/397.2; 204/159
[58] Field of Search ...................................... 260/397.2

[56] References Cited

FOREIGN PATENT DOCUMENTS 56-090082 12/1979 Japan ................................ 260/397.2

OTHER PUBLICATIONS

Chemical Abstracts 90 133429b (1979).
Chemical Abstracts 83 53688a (1975).
Chemical Abstracts 88 69462m (1978).
Proc. Natl. Acad. Sci. (USA) 75 (3), 1374–1378 (1978).

*Primary Examiner*—Elbert L. Roberts
*Attorney, Agent, or Firm*—Browdy and Neimark

[57] ABSTRACT

There are disclosed 6,19-epidioxyvitamin $D_3$ derivatives which are represented by the formula

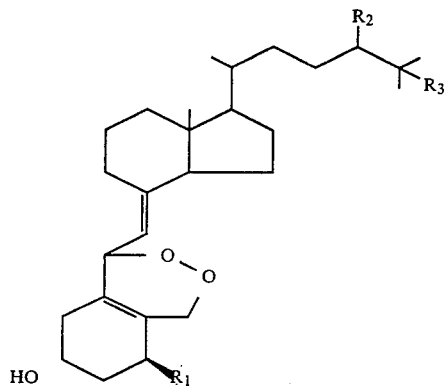

wherein $R_1$, $R_2$ and $R_3$ are each a hydrogen atom or a hydroxyl group; when $R_1$ is a hydrogen atom, $R_2$ represents a hydroxyl group and $R_3$ is a hydrogen atom or a hydroxyl group; when both $R_1$ and $R_2$ represent a hydroxyl group, $R_3$ is a hydrogen atom or a hydroxyl group; and when $R_1$ is a hydroxyl group and $R_2$ is a hydrogen atom, $R_3$ represents a hydroxyl group. The compounds are highly capable of inducing differentiation of human myeloid leukemia cells with minimum effects on calcium metabolism and are useful as an agent to treat leukemia.

4 Claims, No Drawings

NOVEL VITAMIN D3 DERIVATIVES AND PROCESS FOR PRODUCING THE SAME

FIELD OF THE INVENTION

The present invention relates to 6,19-epidioxyvitamin $D_3$ derivatives of formula (I):

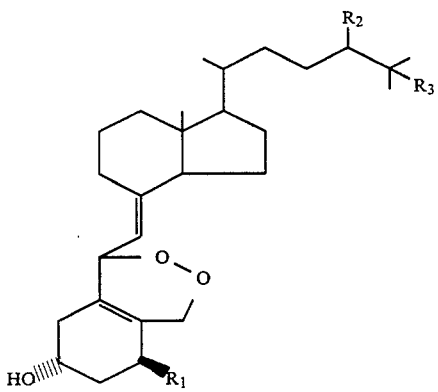

(wherein $R_1$, $R_2$ and $R_3$ are each a hydrogen atom or a hydroxyl group; when $R_1$ is a hydrogen atom, $R_2$ represents a hydroxyl group and $R_3$ is a hydrogen atom or a hydroxyl group; when both $R_1$ and $R_2$ represent a hydroxyl group, $R_3$ is a hydrogen atom or a hydroxyl group; and when $R_1$ is a hydroxyl group and $R_2$ is a hydrogen atom, $R_3$ represents a hydroxyl group).

BACKGROUND OF THE INVENTION

As a result of the studies by DeLuca and Kodicek on the separation and identification of the metabolites of vitamin $D_3$ and on its metabolism, it has been established that vitamin $D_3$ is first hydroxylated (at 25-position) in the liver to form 25-hydroxyvitamin $D_3$, then is hydroxylated (at 24R-position or at 1α-position) in the kidney to form 1α,25-dihydroxyvitamin $D_3$ and 24R,25-dihydroxyvitamin $D_3$ having hormone activity. It is also well known that these metabolites and other synthetic analogs such as 1α-hydroxy-vitamin $D_3$ thereof enhance intestinal calcium transport and bone mineral mobilization and are useful as therapeutic agents to treat the diseases caused by various disorders in calcium metabolism.

A recent study based on experiments with a myeloid leukemia cell line (M1) isolated from an SL mouse with myeloid leukemia has revealed that the above named vitamin $D_3$ derivatives can induce differentiation of myeloid leukemia cells and that they are at least about 100 times as potent as dexamethasone the most potent inducer ever known [Proc. Natl. Acad. Sci. U.S.A. 78, 4990 (1981)]. Sachs [Brit. J. Haematol., 40, 509 (1978)] and Hozumi ["Gan to Kagaku-ryoho (Cancer and Chemotherapy)", 8(1), 9, (1981)] have suggested that compounds capable of inducing differentiation of myeloid leukemia cells can be used to treat leukemia and that use of these compounds is promising as a supplement to the conventional chemotherapy and immunotherapy. But having a very great ability to induce differentiation, these derivatives also have significant effects on calcium metabolism in vivo, and an overdose of them may cause hypercalcemia. So, the derivatives are not completely satisfactory for use as a drug to treat leukemia which sometimes requires continuous administration of the drug in high dose.

SUMMARY OF THE INVENTION

The present inventors have made various studies on vitamin $D_3$ derivatives and have found that 6,19-epidioxy-vitamin $D_3$ derivatives are highly capable of inducing differentiation of human myeloid leukemia cells with minimum effects on calcium metabolism and that hence, they are useful as an agent to treat leukemia.

DETAILED DESCRIPTION OF THE INVENTION

The ability of the compounds (I) of the present invention to induce differentiation of human myeloid leukemia cells was determined by the following method.

HL-60 cells (human myeloid leukemia cell line) were cultured at 37° C. in RPMI 1640 medium (GIBCO, Grand Island, NY) supplemented with 10% heat-inactivated fetal calf serum (Flow Laboratories, Rockville, MD) and 100 U/ml of penicillin and 100 μg/ml of streptomycin in a humidified atmosphere of 5% $CO_2$ in air. Cells were inoculated at $1 \times 10^5$ cells/ml and incubated with various concentrations of inducing compounds. The differentiation-associated properties were tested 3 days after inoculation. The formation of Fc and C3 rosettes was assayed according to the method of Lotem and Sachs Int. J. Cancer 15, 731 (1975) using sheep erythrocytes coated with rabbit anti-sheep erythrocytes antibody, or with the antibody and mouse complement, respectively. The percentage of cells with a rosette to which at least 5 erythrocytes were bound was counted with a hemocytometer. At least 200 cells were counted. Phagocytic activity was measured according to the method of Collins et al. Proc. Natl. Acad. Sci. U.S.A. 75, 2458 (1978). Cells were suspended at a concentration of $2 \times 10^6$ cells/ml in RPMI 1640 medium supplemented with 10% fetal calf serum and 10% human AB serum. *Candida albicans* were washed with saline and added to the cell suspension at a final concentration of $4 \times 10^6$/ml. The suspension was incubated at 37° C. for 30 min. The percentage of cells that had phagocytosed at least one Candida was counted with a hemocytometer.

The results of the experiment are shown in the following table, wherein Ia to If for the chemicals' names are keyed to the symbols used in Examples 1 to 3.

TABLE

| Chemicals added | Concentration (ng/ml) | Phagocytic Cells (%) | C3 receptor (%) |
| --- | --- | --- | --- |
| control | — | 3.8 | 9.9 |
| Ia | 25 | 14.9 | 14.4 |
|  | 250 | 46.5 | 37.4 |
| Ib | 25 | 20.0 | 20.8 |
|  | 250 | 42.7 | 40.0 |
| Ic | 25 | 20.0 | 22.7 |
|  | 250 | 47.5 | 41.8 |
| Id | 25 | 14.9 | 16.5 |
|  | 250 | 38.0 | 42.6 |
| Ie | 50 | 28.0 | 28.0 |
|  | 500 | 60.3 | 47.1 |
| If | 50 | 16.0 | 23.9 |
|  | 500 | 54.3 | 46.3 |

The influence of the compounds of this invention upon calcium metabolism was determined by the following Experiment.

EXPERIMENT

Weanling Sprague Dawley male rats weighing 45 to 50 g were fed on Diet 11 and deionized water under an incandescent lamp for a period of 6 weeks. They were administered orally a solution of each compound in MCT (medium chain triglyceride of The Nisshin Oil Mills, Ltd.) once a day. The animals were starved, beheaded and bled to obtain blood samples. The duodenum was removed from each animal and checked for $^{45}$Ca absorption by the inverted intestimal tract method [Amer. J. Physics., 216, 1351 (1969)]. Plasma was separated from the blood samples and the contents of calcium and inorganic phosphorus were determined by the OCPC method [Am. J. Clin. Path., 45, 290 (1966)] and the method of Peel and Loughman [Biochem. J., 65, 709 (1957)], respectively. The compounds of the present invention were far less capable of transporting calcium from the intestinal tract than known vitamin D$_3$ compounds such as 1α-hydroxyvitamin D$_3$ and 1α,25-dihydroxy-vitamin D$_3$. The compounds had also a very weak effect on the concentrations of phosphorus and calcium in plasma.

The compounds of formula (I) of the present invention are novel and they include 6,19-epidioxy-9,10-seco-cholesta-5(10),7-dien-3β,24-diol, 6,19-epidioxy-9,10-secocholesta-5(10),7-dien-1α,3β,24-triol, 6,19-epidioxy-9,10-secocholesta-5(10),7-dien-1α,3β,24,25-tetraol and 6,19-epidioxy-9,10-secocholesta-5(10),7-dien-1α,3β,25-triol. These compounds can be prepared by subjecting corresponding vitamin D$_3$ compounds, say, 24-hydroxyvitamin D$_3$, 1α,24-dihydroxyvitamin D$_3$, 1α,24,25-trihydroxyvitamin D$_3$ and 1α,25-dihydroxyvitamin D$_3$ to photosensitized oxidation. This can be done by illuminating the corresponding vitamin D$_3$ compounds with visible light emitting sources such as a halogen lamp or tangsten lamp in oxygen or air as they are dissolved in an inert organic solvent such as methanol, ethanol or propanol in the presence of an organic pigment such as Rose Bengal, Eosine or methylene blue. The illumination period preferably continues until the vitamin D$_3$ compounds are no longer present in the reaction system. The compounds (I) can be isolated from the reaction mixture by a conventional method, such as distilling off the solvent followed by column chromatography. The end compounds (I) have an asymmetric carbon atom at 6- or 24-position, and in each case, they include 2 to 4 optical isomers.

The present invention is now described in greater detail by reference to the following examples which are given here for illustrative purposes only and are by no means intended to limit its scope.

EXAMPLE 1

A mixture of 24R-hydroxyvitamin D$_3$ (2.0 mg) and Rose Bengal (10 mg) was dissolved in a mixed solvent consisting of benzene (24 mg) and ethanol (6 ml), and after bubbling oxygen the solution was illuminated with a halogen lamp (200 W) for 40 minutes under cooling with ice. Argon was passed through the reaction mixture, which was subsequently washed with water, dried on sodium sulfate and had the solvent distilled off. The residue was subjected to column chromatography (solvent: 20% ethyl acetate-benzene) on silica gel, whereupon (6R,24R)-6,19-epidioxy-9,10-secocholesta-5(10),7-dien-3β,24-diol (Ia) and (6S,24R)-6,19-epidioxy-9,10-secocholesta-5(10),7-dien-3β,24-diol (Ib) were obtained.

(6R,24R)-form (Ia)

NMR (CDCl$_3$)δ: 0.59 (3H,s), 3.36 (1H,m), 4.12 (1H,m), 4.40 (1H,d, J=16 Hz), 4.48 (1H,d, J=16 Hz), 4.94 (1H,d, J=9 Hz), 5.22 (1H,d, J=9 Hz).

Mass m/e: 432 (M+), 414, 396, 287, 285, 151.

(6S,24R)-form (Ib)

NMR (CDCl$_3$)δ: 0.59 (3H,s), 3.34 (1H,m), 3.97 (1H,m), 4.22 (1H,d, J=16 Hz), 4.64 (1H,d, J=16 Hz), 4.83 (1H,d, J=9 Hz), 5.27 (1H,d, J=9 Hz).

Mass m/e: 432 (M+), 414, 396, 287, 285, 151.

EXAMPLE 2

A mixture of 1α,24R-dihydroxyvitamin D$_3$ (660 μg) and Rose Bengal (20 mg) was dissolved in ethanol (15 ml), and after bubbling oxygen the solution was illuminated with a halogen lamp (200 W) for one hour under cooling with ice. Argon was passed through the reaction mixture, ethanol distilled off and the residue was dissolved in ethyl acetate. The solution was washed with water, the ethyl acetate layer dried over sodium sulfate and the solvent was distilled off. The residue was subjected to column chromatography (solvent: hexane/chloroform/methanol=30/70/3) on Sephadex LH-20 (6 g). Fractions 22 to 30 (3 g for each fraction) were concentrated into 358 g of a residue. The residue was subjected to high-pressure liquid chromatography (column: Lichrosorb, eluant: 20% isopropanol-hexane), whereupon two isomers with different degrees of polarity of (24R)-6,19-epidioxy-9,10-secochlesta-5(10),7-dien-1α,3β,24-triol having different configurations at 6-position, were obtained, and the yield of one compound (Ic) having a weaker polarity was 78 μg and that of the other compound (Id) having a stronger polarity was 310 μg.

Mass spectra for the two compounds: m/e: 430 (M-18), 412, 394, 379.

EXAMPLE 3

A mixture of 1α,25-dihydroxyvitamin D$_3$ (840 μg) and Rose Bengal (20 mg) was dissolved in 15 ml of ethanol (J.P. 10th ed.), and after bubbling oxygen the solution was illuminated with a halogen lamp (200 W) for 1.5 hours. The solvent was distilled off under vacuum and the residue was purified by column chromatography on silica gel, whereupon two isomers with different degrees of polarity and having different configurations at 6-position were obtained, and the yield of one compound (Ie) having a weaker polarity was 150 μg and that of the other compound (If) having a stronger polarity was 310 μg.

Data for compound Ie

Mass m/e: 430 (M+-18), 412, 394, 379.

UV (95% ethanol): no absorption maximum beyond 210 nm.

Data for compound If

Mass m/e: 430 (M+-18), 412, 394, 379.

UV (95% ethanol): no absorption maximum beyond 210 nm.

What is claimed is:

1. A 6,19-epidioxyvitamin D$_3$ derivative of the formula:

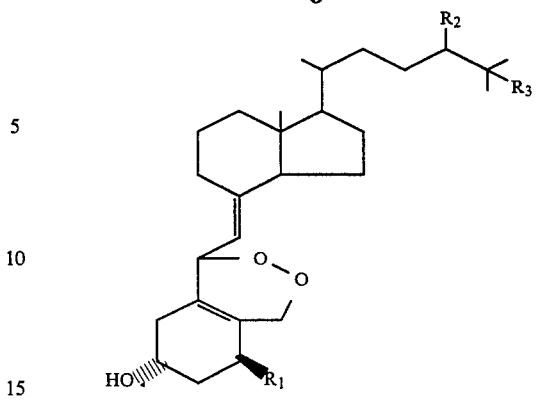

(wherein $R_1$, $R_2$ and $R_3$ are each a hydrogen atom or a hydroxyl group; when $R_1$ is a hydrogen atom, $R_2$ represents a hydroxyl group and $R_3$ is a hydrogen atom or a hydroxyl group; when both $R_1$ and $R_2$ represent a hydroxyl group, $R_3$ is a hydrogen atom or a hydroxyl group; and when $R_1$ is a hydroxyl group and $R_2$ is a hydrogen atom, $R_3$ represents a hydroxyl group).

2. A compound according to claim 1 wherein the 6,19-epidioxyvitamin $D_3$ derivative is 6,19-epidioxy-9,10-secocholesta-5(10),7-dien-3β,24-diol.

3. A compound according to claim 1 wherein the 6,19-epidioxyvitamin $D_3$ derivative is 6,19-epidioxy-9,10-secocholesta-5(10),7-dien-1α,3β,24-triol.

4. A compound according to claim 1 wherein the 6,19-epidioxyvitamin $D_3$ derivative is 6,19-epidioxy-9,10-secocholesta-5(10),7-dien-1α,3β,25-triol.

* * * * *